(12) United States Patent
Kotuljac et al.

(10) Patent No.: US 9,642,656 B2
(45) Date of Patent: May 9, 2017

(54) INTRAMEDULLARY LOCKING BONE SCREW FOR FIXING THE METATARSOPHALANGEAL JOINT OF THE BIG TOE IN FOOT SURGERY

(71) Applicant: ZIMMER GMBH, Winterthur (CH)

(72) Inventors: Vladko Kotuljac, Schoemberg (DE); Michael Vitek, Vienna (AT)

(73) Assignee: ZIMMER GMBH (CH)

( * ) Notice: Subject to any disclaimer, the term of this patent is extended or adjusted under 35 U.S.C. 154(b) by 0 days.

(21) Appl. No.: 14/382,993

(22) PCT Filed: Mar. 6, 2013

(86) PCT No.: PCT/EP2013/054532
§ 371 (c)(1),
(2) Date: Sep. 4, 2014

(87) PCT Pub. No.: WO2013/131974
PCT Pub. Date: Sep. 12, 2013

(65) Prior Publication Data
US 2015/0088136 A1   Mar. 26, 2015

(30) Foreign Application Priority Data
Mar. 8, 2012 (DE) .................. 10 2012 101 978

(51) Int. Cl.
*A61B 17/70* (2006.01)
*A61B 17/72* (2006.01)
(Continued)

(52) U.S. Cl.
CPC ...... *A61B 17/7291* (2013.01); *A61B 17/7233* (2013.01); *A61B 17/848* (2013.01);
(Continued)

(58) Field of Classification Search
CPC .. A61B 17/864; A61B 17/8605; A61B 17/863
USPC ...................... 606/300–320, 62–68
See application file for complete search history.

(56) References Cited

U.S. PATENT DOCUMENTS 4,175,555 A   11/1979   Herbert
5,364,400 A * 11/1994   Rego, Jr. ............ A61B 17/8645
                                                    606/304
(Continued)

FOREIGN PATENT DOCUMENTS

DE       2807364 A1    8/1978
DE      19857279 A1    6/2000
(Continued)

OTHER PUBLICATIONS

"International Application Serial No. PCT/EP2013/054532, English Translation of Annexed Submission and Amended Claims filed on Jun. 16, 2014", 6 pgs.
(Continued)

*Primary Examiner* — Mary Hoffman
*Assistant Examiner* — Tara R Carter
(74) *Attorney, Agent, or Firm* — Schwegman Lundberg & Woessner, P.A.

(57) ABSTRACT

The invention relates to an intramedullary locking bone screw for fixing the metatarsophalangeal joint of the big toe in foot surgery that can be completely received in the bone, said locking bone screw extending along a longitudinal axis (L), with a first outside thread section (6) having a first thread pitch and with at least one second outside thread section (7), preferably designed to be self-tapping, having a pitch that is different from the first thread pitch. According to the invention, at least one fixing channel (K1) penetrating the bone screw (1) for receiving fixing means is provided in the second outside thread section (7), extending at an angle, preferably perpendicular in relation to the longitudinal axis
(Continued)

(L), and a second fixing channel (K2) penetrating the bone screw (I) arranged at an axial distance from the first fixing channel (K1) in the outside thread section (6) for receiving fixing means is provided in the first outside thread section, and a first longitudinal centre axis of the first fixing channel (K1) is arranged offset in the circumferential direction of the bone screw (1) at an angle, preferably 90° in relation to a second longitudinal centre axis of the second fixing channel (K2).

12 Claims, 1 Drawing Sheet

(51) Int. Cl.
*A61B 17/84* (2006.01)
*A61B 17/86* (2006.01)
*A61F 2/42* (2006.01)

(52) U.S. Cl.
CPC .......... *A61B 17/863* (2013.01); *A61B 17/864* (2013.01); *A61B 17/8605* (2013.01); *A61F 2002/4235* (2013.01)

(56) References Cited

U.S. PATENT DOCUMENTS

| | | | | |
|---|---|---|---|---|
| 5,456,685 | A | * | 10/1995 | Huebner ............ A61B 17/8605 411/311 |
| 5,964,768 | A | | 10/1999 | Huebner |
| 6,030,162 | A | * | 2/2000 | Huebner ............ A61B 17/1682 411/263 |
| 6,306,140 | B1 | | 10/2001 | Siddiqui |
| 2007/0233123 | A1 | * | 10/2007 | Ahmad ................ A61B 17/863 606/307 |
| 2011/0082508 | A1 | | 4/2011 | Reed |

FOREIGN PATENT DOCUMENTS

| | | |
|---|---|---|
| EP | 1354562 A1 | 10/2003 |
| EP | 1378205 A1 | 1/2004 |
| WO | WO-2004014243 A1 | 2/2004 |
| WO | WO-2004043277 A1 | 5/2004 |
| WO | WO-2008003433 A1 | 1/2008 |
| WO | WO-2013131974 A1 | 9/2013 |

OTHER PUBLICATIONS

"International Application Serial No. PCT/EP2013/054532, International Preliminary Report on Patentability mailed Sep. 12, 2014", 7 pgs.

"International Application Serial No. PCT/EP2013/054532, International Search Report mailed Jun. 7, 2013", (W/ English Translation), 7 pgs.

"International Application Serial No. PCT/EP2013/054532, Written Opinion mailed Jun. 7, 2013", (English Translation), 4 pgs.

* cited by examiner

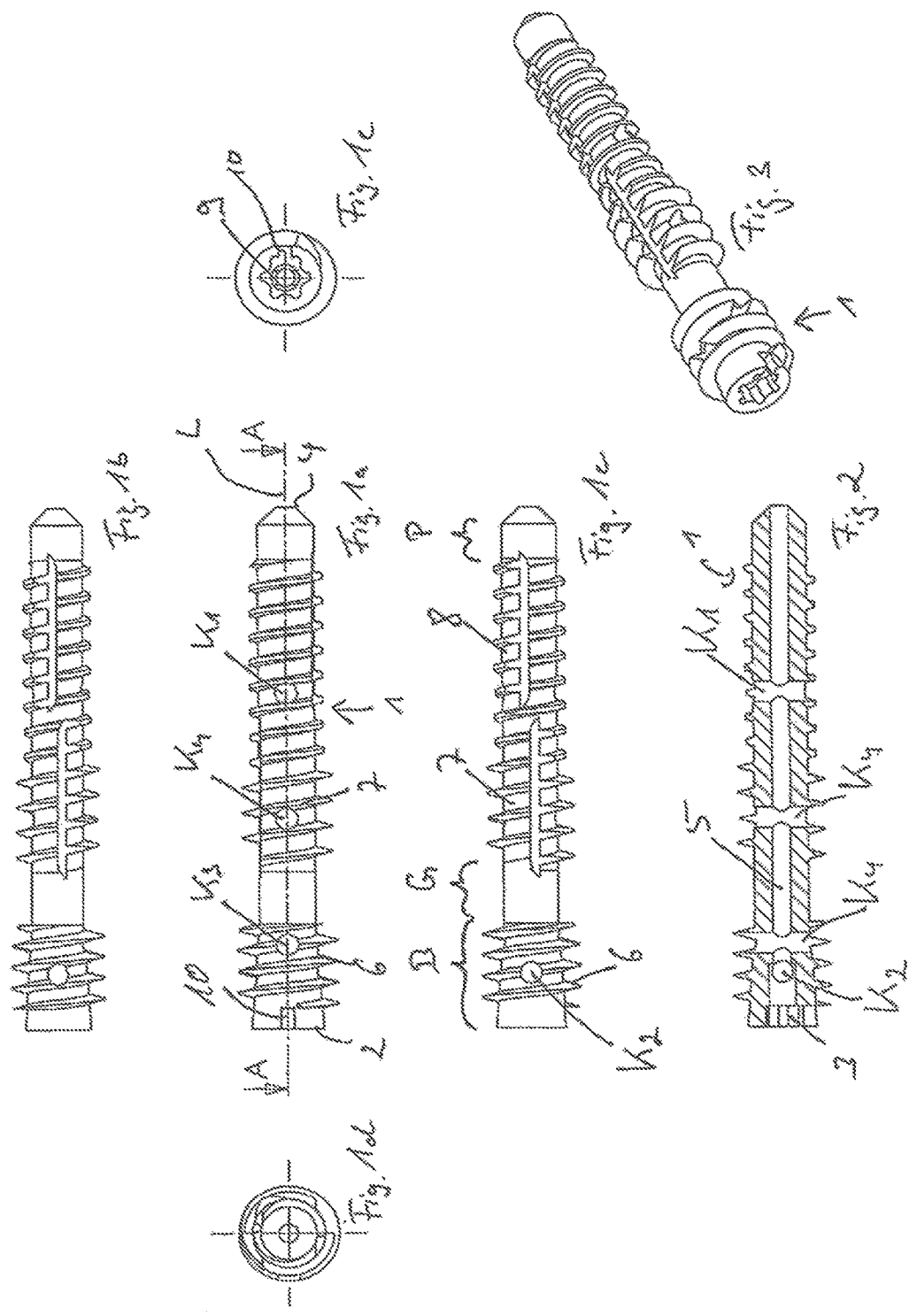

INTRAMEDULLARY LOCKING BONE SCREW FOR FIXING THE METATARSOPHALANGEAL JOINT OF THE BIG TOE IN FOOT SURGERY

PRIORITY APPLICATION

This is a U.S. National Stage Application under 35 U.S.C. 371 from International Application No. PCT/EP2013/054532, filed Mar. 6, 2013, published on Sep. 12, 2013 as WO2013/131974A1, which claims the benefit of priority to German Application No. 102012101978.9, filed on Mar. 8, 2012, the benefit of priority of each of which is claimed hereby, and each of which are incorporated by reference herein in its entirety.

The invention relates to an intramedullary locking bone screw for fixing the metatarsophalangeal joint of the big toe in foot surgery in accordance with claim 1, which extends along a longitudinal axis, having a first outer threaded section having a first thread pitch and having at least one second outer threaded section having a second thread pitch differing from the first thread pitch and preferably formed in a self-tapping manner.

So far bone plates were used for the arthrodesis of the metatarsophalangeal joint of the big toe which were screwed from the outside to the phalanges and the metatarsals. Due to the high loads of the metatarsophalangeal joint of the big toe of the first metatarsal, deformation of the bone plate can arise for the known solution and in this way lead to prolonged healing processes, as well as to mal alignments.

From the DE 28 07 364 A1 a bone screw generally configured as a compression screw is known which has two outer threaded sections having thread pitches differing from one another. The known bone screw is not specifically conceived for foot surgery and has the problem of a not continuously defined positioning which is problematic in particular in the foot region due to the loads arising there.

From the EP 1 354 562 A1 a bone fixation system is known comprising a screw configured as a head screw and in this way is not completely receivable in the bone, the screw having an axially continuous outer thread of constant pitch, wherein a bone compression can only be achieved from the outside with a large demand in effort, in that the head of the bone screw is pressed onto a part of the fracture, whereas the thread of the screw is screwed into the other part of the fracture. In this instance, the effective compression is inadequate. Furthermore, soft tissue irritation is brought about due to the screw head and an inferior healing success is possibly achieved due to this. The known bone screw has lateral fixing passages which are all arranged at the same circumferential angle.

From the WO 2008/0034333 A1 an implant for osteosynthesis of a near base osteotomy of a metatarsal is known. In order to be able to achieve a compressive effect with the known implant, which is free of outer threads, the implant is provided with fixing passages for the reception of fixing screws in the forward region, the fixing passages being arranged displaced in the peripheral direction, wherein the fixing screws in this instance merely take on the holding function of the thread of a screw, whereas the compression is achieved at a different position by means of a transverse screw.

Starting from the state of the art the invention is based on the object of providing an improved implant for the arthrodesis of the metatarsophalangeal joint of the big toe of the first metatarsal which is characterized by a high robustness. In particular the aforementioned disadvantages should be avoided.

This object is satisfied by a intramedullary locking bone screw in foot surgery having the features of claim 1. Advantageous embodiments of the invention are stated in the subordinate claims.

The invention is based on the idea of using a locking bone screw which can be arranged intramedullarily for the fixation of the joint of the big toe in the human foot, the locking bone screw being characterized by at least two outer threaded sections having a different pitch in order to achieve a compression between the phalanges and the metatarsals. Moreover, it is provided in accordance with the invention that the bone screw has at least one fixing passage passing through the bone screw at an angle, preferably at a right angle, with respect to the longitudinal axis, into which fixing means can be introduced from the outside, in particular into which a fixing screw can be screwed in order to fix the bone screw in the desired position of installation and to secure this against rotation.

Preferably, the axial extent of the bone screw is selected from a value range of between 40 and 60 mm. Very particularly preferably, the axial extent amounts to approximately 50 mm. Moreover, it is particularly expedient when the maximum outer diameter of the bone screw amounts to less than 15 mm, and preferably amounts to less than 12 mm. Very particularly preferably, the maximum outer diameter is selected from a value range of between 6 mm and 11 mm, preferably of between 7 and 10 mm. Even more preferably it amounts to approximately 9 MM.

The bone screw in accordance with the invention is preferably used for the indications Hallux rigidus stages III and IV, as well as for extremely deviating Hallux valgus.

Particularly advantageous uses of the bone screw configured in accordance with the concept of the invention is that no soft tissue problems arise in contrast to the bone plates so far used, as the bone screw is completely received in the bone. Following the operation, a full load is possible straight away using a comfort shoe. Moreover, an extremely rigid compression arthrodesis results which does not loose the compression from which a rapid bone healing results due to the locking with the aid of the fixing means.

In accordance with the invention it is provided to provide at least one second fixing passage passing through the bone screw for the reception of further fixing means, in particular a (further) fixing screw in addition to the first fixing passage in order to be able to fix the bone screw at at least two axially spaced apart positions by screwing in a lateral fixing screw and/or in order to have a larger flexibility during the operation and to not be limited to a single fixing position. It has been found to be particularly practicable when at least two fixing passages are not aligned in parallel but rather have inputs and outputs which are displaced with respect to one another in the circumferential direction. In other words, it is preferred when at least two fixing passages are arranged rotated with respect to one another by an angle, of preferably 90°, in order to enable a fixing of the bone screw from different lateral directions.

In this connection, the first and the second fixing passage arranged displaced with respect to one another in the circumferential direction are arranged distributed at the first and the second outer threaded section. In other words, the first fixing passage is present in the second outer threaded section and the second fixing passage arranged displaced in the circumferential direction with respect to this is present in the first outer threaded section 6, preferably in the rear outer threaded section. The distribution of the fixing passages arranged displaced with respect to one another in the circumferential direction at the two outer threaded sections having a pitch different with respect to one another, enables a good accessibility of the fixing passages from different circumferential positions and ensures an ideal arrangement secured against rotation.

The complete insertability of the bone screw in accordance with the invention into the human bone is preferably achieved thereby that the screw has no stepped screw head. Rather more it is preferably provided that a conical contour of a screw core continues starting from a cylindrical section up to the axial rear end of the bone screw.

In the case in which more than two lateral fixing passages are provided, which is preferred, it is particularly advantageous when at least two, preferably three fixing passages are aligned in parallel to one another. It is even further preferred when (preferably exclusively) a rearmost fixing passage is rotated with respect to other fixing passages in the circumferential direction, preferably by 90°, even more preferably this is rotated with respect to all other fixing passages.

In order to enable a targeted insertion of the bone screw into the bone of the first metatarsal of a human foot, it is particularly expedient when the bone screw is cannulated in order to be able to receive a bore wire, preferably having a diameter of 1.6 mm. Wherein it is even further preferred when the first fixing passage and/or the second fixing passage, preferably all fixing passages cuts/cut the central through passage, in particular at an angle of 90°.

In order to simplify the insertion of the bone screw into the foot bone and in order to moreover achieve a good fixation and/or a good holding of the bone screw in the first metatarsal of the human foot, it is particularly expedient when the outer diameter of the first and of the second outer thread is of different size, wherein it is even more preferable, when the first outer threaded section is provided behind the second outer threaded section, this means that it is closer to, preferably directly adjacent to, a preferably provided (rear) drive of the bone screw.

In order to ensure an ideal compression of the bone segment/bone sections to be connected to one another, it is particularly expedient when the core diameter of the bone screw changes in the region of the first outer threaded section over the longitudinal extent of the bone, wherein it is even more preferable when the core diameter tapers in this region from the rear to the front, and is in particular conically contoured.

It is even more preferable, when the sleeve contour of the first outer thread is not adapted to the change in core diameter, but rather is cylindrically contoured over the axial extent, at least over the largest part of the axial extent. It is particularly expedient, when the region of the changing core diameter, in particular the conically contoured region of the core, forms a rear section of the screw and/or is arranged in a rear region of the screw, wherein it is even more preferable when a core diameter section adjacent thereto is cylindrically contoured. Preferably, the axial extent of the cylindrically contoured core diameter section amounts to a multiple, in particular to a three- to six-fold, of the axial extent of the section of the changing core diameter. Preferably, the conical angle of the conical section, measured between a conical jacket surface and the longitudinal middle axis of the screw, amounts to approximately 2 and 6°, and preferably amounts to 4°.

It is very particularly preferred when the first outer thread diameter is arranged in the region of the rear bone screw end having a drive and has a smaller extent than the second outer threaded section, which is preferably spaced apart by means of a thread-free axial section. Preferably the first outer threaded section totally has the smallest pitch—with respect to all outer threaded sections. It has been found to be particularly expedient, when the first outer threaded section is configured in a self-tapping manner.

Ideal fixing results and/or an ideal assembly facilitation is achieved when at least one third, preferably only one third, outer threaded section is provided in addition to the first and the second outer threaded section, the third outer threaded section differing from the further outer threaded sections (first and second outer threaded sections) by at least one feature of geometry. Thus, it is particularly expedient, when the third outer threaded section has a smaller outer diameter than the first and/or the second outer threaded section. Preferably, the core diameter in the region of the second and third outer threaded sections is constant. It is even further preferred when the axial extent of the third outer threaded section is larger than that of the first outer threaded section and/or of the second outer threaded section. Ideally, the second outer threaded section is axially arranged between the first and the third outer threaded section, wherein the third outer threaded section even more preferably forms a front-most outer threaded section. In this connection it is particularly expedient, when a thread-free axial section adjoins at the front at the third outer threaded section.

The pitch of the first outer threaded section is very particularly preferably selected from a value range of between 1.5 and 2 mm and even more preferably amounts to 2 mm. The pitch of the second outer threaded section is very particularly preferably selected from a value range of between 2.0 mm and 3.0 mm and preferably amounts to approximately 2.4 mm. The pitch of an optional third outer threaded section is even more preferably selected from a value range of between 2.0 mm and 3.0 mm and preferably amounts to 2.4 mm.

It is ideal when the second and the third outer threaded section directly transition into one another. It has been found to be particularly expedient, when one of the aforementioned fixing passages is provided in each of the three outer threaded sections, wherein two fixing passages are preferably provided in the first outer threaded section rotated with respect to one another by an angle in the circumferential direction, in particular rotated by 90°.

In order to simplify the positioning of the bone screw for the surgeon and/or in order to position the fixing passages at defined circumferential positions, a corresponding marking is provided with advantage in an embodiment of the invention at the rear end face of the bone screw and indeed in the form of a transverse passage open towards the rear and extending in the radial direction in the shape of a central rear drive recess in a lateral direction, this means in the radial direction up to the outer periphery of the bone screw, wherein the transverse passage is preferably configured in such a way that fixing means can be temporarily introduced into this from the radial direction from the outside, in particular a fixing screw or a fixing pin, in order to be able to exactly align a target device for the insertion of the fixing means in the fixing passages relative to the bone screw with respect to a preferably used target device by means of which fixing screws can be introduced into the preferably inner thread free fixing passage.

Further advantages, features and particulars of the invention result from the subsequent description of preferred embodiments, as well as with reference to the drawing.

These show in:

FIG. 1a to FIG. 1e various illustrations of a preferred embodiment of an intramedullary locking bone screw for fixing the metatarsophalangeal joint of the big toe in the first metatarsal;

FIG. 2 a sectional view along the sectional line A-A in accordance with FIG. 1a; and FIG. 3 a perspective inclined view inclined from behind of the bone screw shown in the aforementioned Figures.

In the Figures like elements having the same function are characterized with the same reference numerals.

In the FIGS. 1a to 3 an intramedullary locking bone screw 1 for the fixation of the metatarsophalangeal joint of the big toe for foot surgery is shown. The bone screw extends from a rear end 2 having a drive 3, configured in this instance as a Torx drive, along a longitudinal axis L up to a front end 4. As results from the sectional view in accordance with FIG. 2, the bone screw 1 is configured cannulated and has an axially through going central through passage 5 for the reception of a Kirschner wire, in the present instance a 1.6 Kirschner wire. In the shown embodiment the axial extent of the bone screw 1 amounts to 50 mm.

In a rear region B, a core diameter of the screw tapers from 6.4 mm to 5 mm from which a conical angle of approximately 4 degrees results. The tapering core diameter extends starting from the rear end 2 by 10 mm to the front. A region having a constant core diameter is adjacent to this rear region B which approximately has four times the length of the rear region B. The bone screw 1 terminates at the front with a conically chamfered front end region.

A first outer threaded section 6 configured in a self-tapping manner is present in the rear region B of the bone screw 1, the first outer threaded section having a cylindrical sleeve contour. A thread-free axial section G adjoins at the front of this first outer threaded section 6, with the axial extent of the thread free section amounting to approximately 5 mm. A second outer threaded section 7, which is different from the first outer threaded section, adjoins at the thread-free section G and which axially transitions into a third outer threaded section 8 at which a further short thread-free section axially adjoins. Both the second, as well as the third outer threaded sections 7, 8 are configured in a self-tapping manner. Corresponding cutting edges are provided for this purpose, wherein the cutting edges of the first, second and third outer threaded section are arranged displaced with respect to one another in the circumferential direction. In the shown embodiment, the outer diameter of the first outer threaded section 6 amounts to 9 mm.

The pitch of which amounts to 2 mm and the axial extent of the first outer threaded section amounts to 8 mm.

The second outer threaded section 7 has an axial extent of 10 mm. The constant outer diameter amounts to 8 mm and the pitch to 2.4 mm. The third outer threaded section has a smaller constant outer diameter of 6.5 mm.

The pitch corresponds to the pitch of the second outer threaded section, this means to 2.4 mm in the illustrated embodiment. The axial extent approximately corresponds to twice the axial extent of the second outer threaded section, this means to 20 mm in the illustrated embodiment.

From the different views it can be recognized that a plurality of fixing passages oriented perpendicular to the longitudinal axis L are provided, namely a first fixing passage K1 in the region of the third outer threaded section 8, a second fixing passage K2 arranged rotated in the circumferential direction by 90° with respect to this, the second fixing passage forming a rearmost fixing passage and being arranged in the region of the first outer threaded section 6. Moreover, two further fixing passages are provided, namely a third fixing passage K3 likewise provided in the region of the first outer threaded section 6 and a fourth fixing passage K4 provided in the region of the second outer threaded section. The fixing passages K1, K3 and K4 are aligned in parallel with respect to one another, axially spaced apart from one another, in the illustrated embodiment they are uniformly spaced apart from one another.

A rear central drive recess 9, in the present instance configured as a Torx recess, is noticeable which is not configured to extend around the full periphery, but rather is laterally opened by means of a transverse passage 10 which is configured open towards the rear. A target device can be exactly aligned with respect to the bone screw 1 via this transverse passage 10 in order to rotationally secure and/or axially fix the bone screw through the insertion of at least one fixing screw into at least one of the fixing passages K1 to K4. Preferably, the fixation takes place in the first metatarsal of the foot as follows: initially a bore wire is introduced plantar into the metatarsal I at the phalanges.

This bore wire is then bored over, preferably with a 6 mm cannulated bore, whereupon the bone screw 1 is turned in via the central bore wire. The preferred assembly of a target device then takes place, wherein the alignment of the bone screw 1 takes place by means of a lateral pin which is introduced from the radial outside into the transverse passage 10.

LIST OF REFERENCE NUMERALS 1 bone screw
2 rear end
3 drive
4 front end
5 through passage
6 first outer threaded section
7 second outer threaded section
8 third outer threaded section
9 drive recess
10 transverse passage
B rear region
G thread-free section
L longitudinal axis
P thread-free axial section
K1 first fixing passage
K2 second fixing passage
K3 third fixing passage
K4 fourth fixing passage

The invention claimed is:

1. An intramedullary locking bone screw for fixing the metatarsophalangeal joint of the big toe in foot surgery which is completely receivable in the bone and which extends along a longitudinal axis, comprising a first outer threaded section having a first thread pitch and having at least one second outer threaded section having a second thread pitch different from the first thread pitch, wherein at least one first fixing passage is provided for the reception of fixation means in the second outer threaded section, the passage extending at an angle with respect to the longitudinal axis and passing through the bone screw;

wherein a second fixing passage for the reception of fixing means is provided which has an axial spacing with respect to the first fixing passage, which is arranged in the first outer threaded section and which passes through the bone screw;

wherein a first longitudinal middle axis of the first fixing passage is arranged at an angle with respect to a second longitudinal middle axis of the second fixing passage in the circumferential direction of the bone screw;

wherein the first outer threaded section is arranged in the region of a rear bone screw end having a drive and a smaller pitch than the second outer threaded section;

wherein a core diameter of the bone screw in the region of the first outer threaded section changes over the longitudinal extent of the bone screw, namely tapers from the rear bone screw end toward a front end of the bone screw;

wherein the core diameter of the bone screw in the region of the first outer threaded section is conically contoured, wherein the conical shape of the core continues starting from a cylindrical section up to the axial rear end of the bone screw;

wherein the conical angle of the conical section of the core, measured between a conical jacket surface and the longitudinal axis of the screw, amounts to between approximately 2° and 6°; and wherein the first outer threaded section has a cylindrical sleeve contour.

2. The bone screw in accordance with claim 1, wherein the bone screw has a non-stepped screw head.

3. The bone screw in accordance with claim 1, further comprising a third fixing passage for the reception of fixing means which passes through the bone screw and which has a third longitudinal middle axis, wherein the third longitudinal middle axis is preferably arranged in parallel to the longitudinal extent of the first or second fixing passages.

4. The bone screw in accordance with claim 3, wherein the bone screw has a through passage for the reception of a Kirschner wire, with the through passage extending along the longitudinal axis.

5. The bone screw in accordance with claim 4, wherein at least one of the first fixing passage, the second fixing passage, and the third fixing passage cuts the through passage at a right angle.

6. The bone screw in accordance with claim 1, wherein a first outer diameter of the first outer threaded section is different from a second outer diameter of the second outer threaded section.

7. The bone screw in accordance with claim 1, further comprising a third outer threaded section configured in a self-tapping manner, the third outer threaded section having a smaller outer diameter than at least one of the first and the second outer threaded sections, or a pitch that corresponds to the pitch of the second outer threaded section, or an axial extent that is larger than that of at least one of the first and the second outer threaded sections, or which axially receives the second outer threaded section, or which directly transitions into the second outer threaded section.

8. The bone screw in accordance with claim 1, wherein the bone screw has a central drive recess in the region of the rear end, and wherein the drive recess is connected at a position to an outer circumferential side of the bone screw via an axially backwardly open transverse passage, with the drive recess being exclusively connected to the outer circumferential side of the bone screw.

9. The bone screw in accordance with claim 1, wherein the second outer threaded section is spaced apart from the first outer threaded section by a thread-free axial section.

10. The bone screw in accordance with claim 1, wherein the second outer threaded section is configured in a self-tapping manner.

11. The bone screw in accordance with claim 1, wherein the first fixing passage extends at a right angle with respect to the longitudinal axis, or wherein the first longitudinal middle axis of the first fixing passage is arranged rotated by an angle of 90° with respect to the second longitudinal middle axis of the second fixing passage in the circumferential direction of the bone screw.

12. An intramedullary locking bone screw for fixing the metatarsophalangeal joint of the big toe in foot surgery which is completely receivable in the bone and which extends along a longitudinal axis, comprising a first outer threaded section having a first thread pitch and having a second outer threaded section having a second thread pitch different from the first thread pitch, wherein at least one first fixing passage is provided for the reception of fixation means in the second outer threaded section, the passage extending at an angle with respect to the longitudinal axis and passing through the bone screw;

wherein a second fixing passage for the reception of fixing means is provided which has an axial spacing with respect to the first fixing passage, which is arranged in the first outer threaded section and which passes through the bone screw;

wherein a first longitudinal middle axis of the first fixing passage is arranged at an angle with respect to a second longitudinal middle axis of the second fixing passage in the circumferential direction of the bone screw;

wherein the first outer threaded section is arranged adjacent to a rear end of the bone screw having a drive, the second outer threaded section is arranged adjacent to a front end of the bone screw, and the first outer threaded section has a smaller pitch than the second outer threaded section;

wherein a core diameter of the first outer threaded section tapers from the rear end of the bone screw toward the front end of the bone screw, thereby defining a conical contour;

wherein the conical contour begins at the rear end of the bone screw and terminates at a front end of the first outer threaded section;

wherein a conical angle, measured between a conical jacket surface of the first outer threaded section and the longitudinal axis of the bone screw, is between approximately 2° and 6°; and wherein the first outer threaded section has a cylindrical sleeve contour.

* * * * *

UNITED STATES PATENT AND TRADEMARK OFFICE
CERTIFICATE OF CORRECTION

PATENT NO. : 9,642,656 B2
APPLICATION NO. : 14/382993
DATED : May 9, 2017
INVENTOR(S) : Kotuljac et al.

It is certified that error appears in the above-identified patent and that said Letters Patent is hereby corrected as shown below:

On the Title Page

In item (30), in "Foreign Application Priority Data", in Column 1, Line 1, delete "10 2012 101 978" and insert --102012101978.9-- therefor On page 2, in item (57), in "Abstract", in Column 1, Line 2, delete "(I)" and insert --(1)-- therefor Signed and Sealed this
First Day of May, 2018

Andrei Iancu
*Director of the United States Patent and Trademark Office*